(12) United States Patent
Kim et al.

(10) Patent No.: US 11,231,395 B2
(45) Date of Patent: Jan. 25, 2022

(54) SMART SCREW

(71) Applicants: Kyungpook National University Industry-Academic Cooperation Foundation, Daegu (KR); Daegu Gyeongbuk Institute of Science and Technology, Daegu (KR); Korea Advanced Institute of Science and Technology, Daejeon (KR)

(72) Inventors: Shin Yoon Kim, Daegu (KR); Jun Young Kim, Daegu (KR); Anna Seo, Daegu (KR); Hee Sung Lee, Daegu (KR); Jae Youn Hwang, Daegu (KR); Sangyeon Youn, Seoul (KR); Jae Suk Choi, Gyeonggi-do (KR); Min Kyu Je, Daegu (KR)

(73) Assignees: Kyungpook National University Industry-Academic Cooperation Foundation, Daegu (KR); Daegu Gyeongbuk Institute of Science and Technology, Daegu (KR); Korea Advanced Institute of Science and Technology, Daegu (KR)

(*) Notice: Subject to any disclaimer, the term of this patent is extended or adjusted under 35 U.S.C. 154(b) by 311 days.

(21) Appl. No.: 16/467,829

(22) PCT Filed: Dec. 8, 2017

(86) PCT No.: PCT/KR2017/014383
§ 371 (c)(1),
(2) Date: Jun. 7, 2019

(87) PCT Pub. No.: WO2018/106057
PCT Pub. Date: Jun. 14, 2018

(65) Prior Publication Data
US 2021/0190730 A1    Jun. 24, 2021

(30) Foreign Application Priority Data

Dec. 9, 2016 (KR) .................. KR10-2016-0167921

(51) Int. Cl.
*A61B 17/86* (2006.01)
*G01N 29/07* (2006.01)
(Continued)

(52) U.S. Cl.
CPC ............. *G01N 29/07* (2013.01); *A61B 17/86* (2013.01); *A61F 2/32* (2013.01); *B06B 1/06* (2013.01);
(Continued)

(58) Field of Classification Search
CPC ... A61B 17/86; A61B 2017/0011; A06B 1/06; A61F 2/32; A61F 2002/488; H02J 50/10; G01B 17/02
See application file for complete search history.

(56) References Cited

U.S. PATENT DOCUMENTS 7,097,662 B2   8/2006 Evans, III et al.
8,029,566 B2  10/2011 Lozier et al.
(Continued)

FOREIGN PATENT DOCUMENTS

JP    2007530083 A    11/2007
KR    101197923 B1    11/2012
(Continued)

*Primary Examiner* — Dinah Baria
(74) *Attorney, Agent, or Firm* — Downs Rachlin Martin PLLC

(57) ABSTRACT

A smart screw according to an embodiment may comprise: a screw main body which penetrates an artificial joint including a shell disposed on a hip joint of an object and a liner disposed on the inner surface of the shell and is then inserted into the hip joint; a transducer including a coupling layer that senses a sound wave signal reflected from the liner, a piezo-electric layer formed to determine a frequency (Continued)

of the sound wave signal, and a sound absorbing layer for absorbing the sound wave signal; and a processing module for generating a sound wave signal toward the liner and receiving the sound wave signal sensed by the coupling layer, measuring the thickness of the liner on the basis of the received sound wave signal, and transferring data about the measured thickness of the liner to the outside.

16 Claims, 6 Drawing Sheets

(51) Int. Cl.
*A61F 2/32* (2006.01)
*B06B 1/06* (2006.01)
*G01B 17/02* (2006.01)
*H02J 50/10* (2016.01)
*A61B 17/00* (2006.01)
*A61F 2/48* (2006.01)

(52) U.S. Cl.
CPC ...... *G01B 17/02* (2013.01); *A61B 2017/0011* (2013.01); *A61B 2017/00221* (2013.01); *A61F 2/488* (2021.08); *G01N 2291/02854* (2013.01); *H02J 50/10* (2016.02)

(56) References Cited

U.S. PATENT DOCUMENTS

| 8,690,929 | B2* | 4/2014 | Stein ................... A61B 5/6846 606/301 |
| 2007/0179739 | A1 | 8/2007 | Donofrio et al. |
| 2013/0079790 | A1 | 3/2013 | Stein et al. |

FOREIGN PATENT DOCUMENTS

| KR | 101368196 | B1 | 2/2014 |
| KR | 20140066193 | A | 5/2014 |
| KR | 20150108694 | A | 9/2015 |
| KR | 20160013847 | A | 2/2016 |
| WO | 2014028742 | A1 | 2/2014 |

* cited by examiner

SMART SCREW

TECHNICAL FIELD

Example embodiments relate to a smart screw.

Background Art

Total hip replacement arthroplasty refers to a surgery conducted to replace, with artificial implants, both acetabulum and femoral head, which is a pelvic bone portion forming a hip joint or a pelvic joint. That is, when a hip joint is severely damaged due to various causes and does not function normally, the arthroplasty may be conducted to remove an original joint portion and insert a hip joint implant including a cup, a liner, and a stem into a body. To reduce a replacement period of the inserted hip joint implant, the liner of the hip joint implant may be made of a special material that may be less frictional and abrasive, and less worn.

For example, Korean Patent Publication No. 10-2014-0066193 discloses "lined femoral cup."

DISCLOSURE OF INVENTION

Technical Goals

An aspect provides a smart screw that may predict a life of a hip joint implant without affecting an activity of a human body.

An aspect also provides a smart screw that may measure a thickness of a liner of a hip joint implant inserted in a human body.

Technical Solutions

According to an example embodiment, there is provided a smart screw including a main screw body configured to penetrate an artificial joint including a shell disposed on a hip joint of an object and a liner disposed on an inner surface of the shell to be inserted into the hip joint, a transducer including a matching layer configured to detect a sound wave signal reflected from the liner, a piezoelectric layer formed to have a preset frequency of the sound wave signal, and a backing layer configured to absorb the sound wave signal, and a processing module configured to generate the sound wave signal towards the liner, receive the sound wave signal detected by the matching layer, measure a thickness of the liner based on the received sound wave signal, and transfer data of the measured thickness of the liner to an outside of the smart screw.

The smart screw may further include a coil disposed to surround the piezoelectric layer, and configured to transmit or receive an electromagnetic wave to or from the outside.

The smart screw may further include a coil provided in the artificial joint and connected to the transducer, and configured to transmit or receive an electromagnetic wave to or from the outside.

The processing module may include a sound wave transmitter-receiver configured to generate the sound wave signal and transfer the generated sound wave signal to the liner, and receive the sound wave signal reflected from the liner through the transducer, a processor configured to analyze the received sound wave signal and obtain the data of the thickness of the liner, and control power, a data transmitter-receiver configured to transmit and receive the data of the thickness of the liner to and from the outside through the coil, and a power unit configured to receive power through the coil and allow the processor to control the power.

The smart screw may further include a transmitting layer formed on an outer side of the transducer and the processing module, and configured to allow the electromagnetic wave to be transmitted to communicate with the coil.

According to another example embodiment, there is provided a smart screw including a main screw body configured to penetrate an artificial joint including a shell disposed on a hip joint of an object and a liner disposed on an inner surface of the shell to be inserted into the hip joint, a transducer disposed in the main screw body and configured to detect a sound wave signal reflected from the liner and receive power from an outside, and a processing module connected to the transducer and configured to measure a thickness of the liner based on the sound wave signal and transfer data of the measured thickness of the liner to the outside.

The processing module may include a sound wave transmitter-receiver configured to generate the sound wave signal and transfer the generated sound wave signal to the liner, and receive the sound wave signal reflected from the liner through the transducer, a processor configured to analyze the received sound wave signal and obtain the data of the thickness of the liner, and control power, a data transmitter-receiver configured to transmit and receive the data of the thickness of the liner to and from the outside through the transducer, and a power unit configured to receive power through the transducer and allow the processor to control the power.

According to still another example embodiment, there is provided a smart screw including a main screw body configured to penetrate an artificial joint including a shell disposed on a hip joint of an object and a liner disposed on an inner surface of the shell to be inserted into the hip joint, a first transducer disposed on a proximal end of the main screw body, a second transducer disposed on a distal end of the main screw body, and a processing module connected to each of the first transducer and the second transducer and configured to obtain data of a thickness of the liner and transmit and receive power to and from an outside.

The first transducer may be configured to detect a sound wave signal reflected from the liner, and the second transducer may be configured to receive power from the outside.

The first transducer may include a first piezoelectric layer formed to have a first frequency band of the sound wave signal, and the second transducer may include a second piezoelectric layer formed to have a second frequency band of the sound wave signal.

The processing module may include a sound wave transmitter-receiver configured to generate the sound wave signal and transfer the generated sound wave signal to the liner, and receive the sound wave signal reflected from the liner through the first transducer, a processor configured to analyze the received sound wave signal and obtain the data of the thickness of the liner, and control power, a data transmitter-receiver configured to transmit and receive the data of the thickness of the liner to and from the outside through the second transducer, and a power unit configured to receive power through the second transducer and allow the processor to control the power.

Advantageous Effects

According to example embodiments described herein, a smart screw may predict a life of a hip joint implant without affecting an activity of a human body.

According to example embodiments described herein, a smart screw may measure a thickness of a linear of a hip joint implant inserted in a human body.

Advantageous effects of the smart screw are not limited to what has been described above, and other effects may be clearly construed by a person having ordinary skill in the art to which the present disclosure pertains (hereinafter "those skilled in the art") from the following description.

BEST MODE FOR CARRYING OUT THE INVENTION

Figure 1:
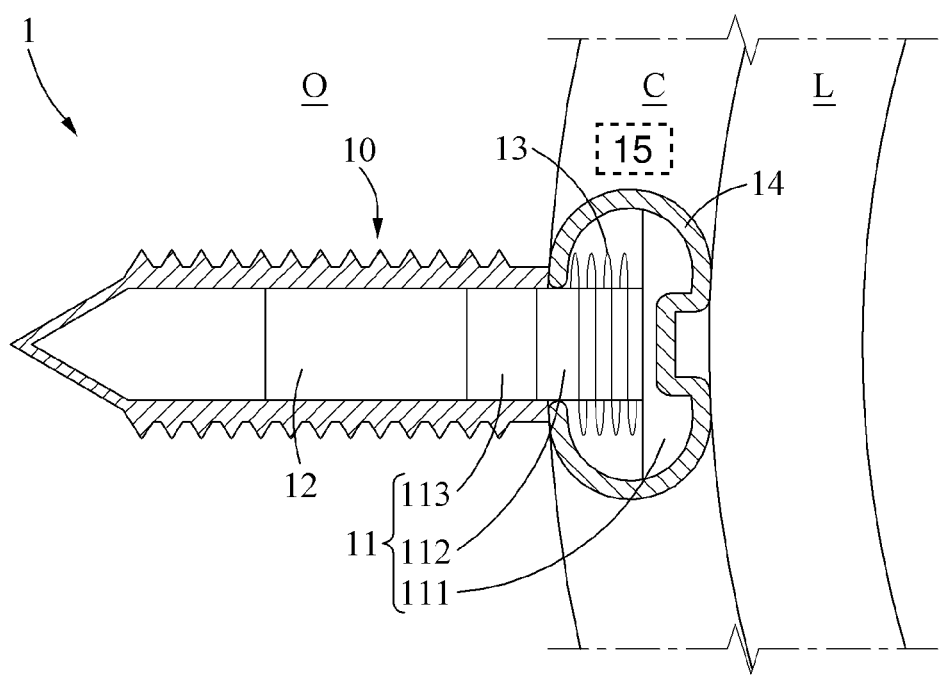
FIG. 1 is a cross-sectional view of an example of a smart screw according to an example embodiment.

Hereinafter, example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, descriptions of features that are known in the art may be omitted for increased clarity and conciseness.

Terms such as first, second, A, B, (a), (b), and the like may be used herein to describe components. Each of these terminologies is not used to define an essence, order, or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application. Also, in the description of example embodiments, detailed description of well-known related structures or functions will be omitted when it is deemed that such description will cause ambiguous interpretation of the present disclosure.

Figure 2:
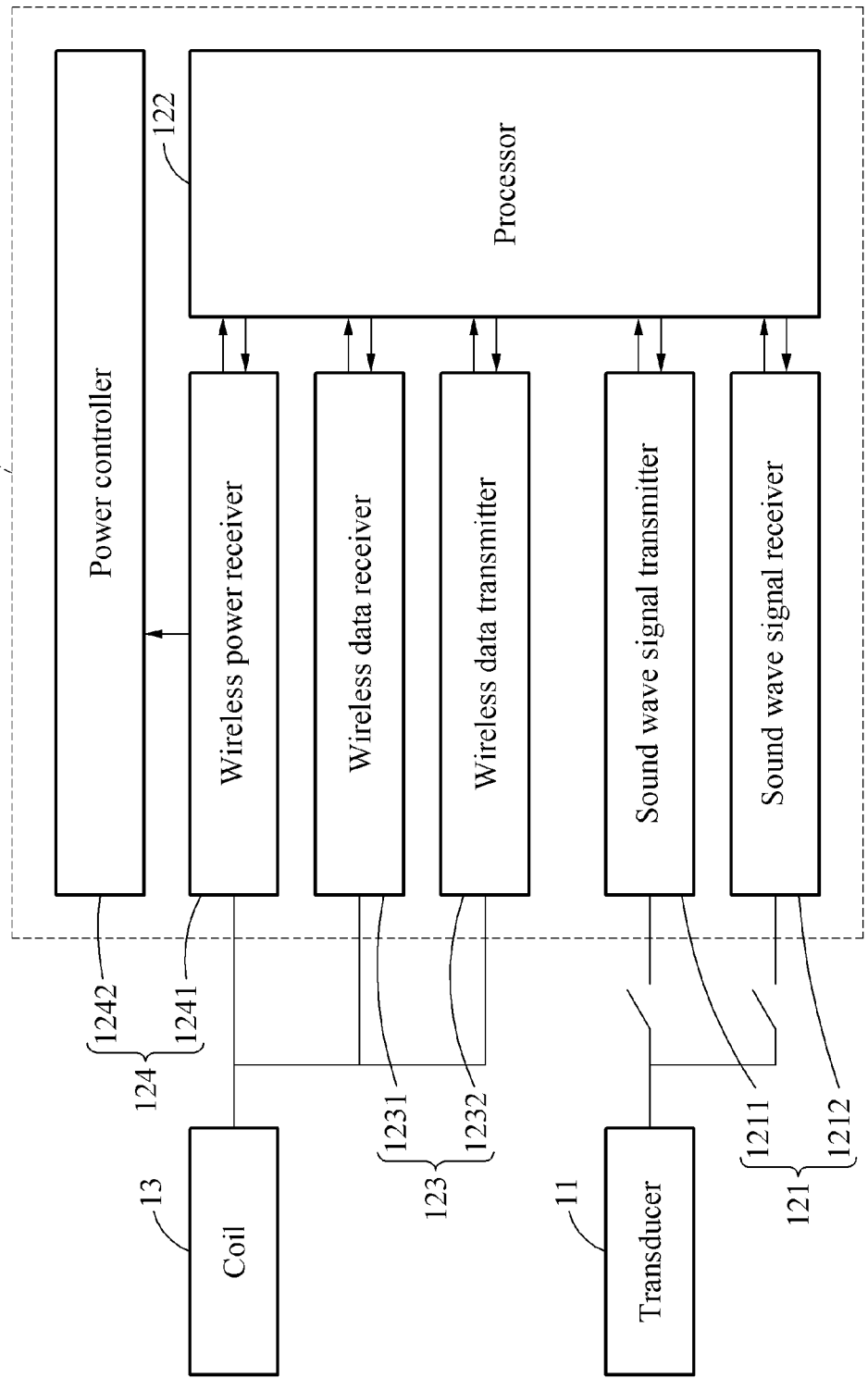
FIG. 2 is a conceptual view of an example of a smart screw according to an example embodiment.

FIG. 1 is a cross-sectional view of an example of a smart screw according to an example embodiment. FIG. 2 is a conceptual view of an example of a smart screw according to an example embodiment.

Referring to FIGS. 1 and 2, a smart screw 1 is used to fix, to a hip joint O of an object, an artificial joint including a shell C to be disposed in the hip joint O and a liner L disposed on an inner surface of the shell C. Although the smart screw 1 is described as being used to fix the artificial joint to be disposed in the hip joint O of the object, a purpose thereof may not be limited thereto and it may also be used to fix an artificial joint to a knee joint, an elbow joint, and an ankle joint. The smart screw 1 includes a main screw body 10 configured to penetrate the artificial joint to be inserted into the hip joint O, a transducer 11, a processing module 12, a coil 13, and a transmitting layer 14.

The transducer 11 is configured to convert a sound wave signal to an electrical signal. The transducer 11 includes a matching layer 111, a piezoelectric layer 112, and a backing layer 113.

The matching layer 111 is configured to detect a sound wave signal reflected from the liner L. For example, the matching layer 111 may detect an ultrasonic signal which is transferred towards the liner L and reflected from the liner L. The piezoelectric layer 112 is formed to have a preset frequency of the sound wave signal. In detail, a thickness of the piezoelectric layer 112 is determined such that a resonant frequency of the sound wave signal is determined. The backing layer 113 is configured to absorb the sound wave signal. The matching layer 111, the piezoelectric layer 112, and the backing layer 113 are sequentially arranged in a direction away from the liner L inside the main screw body 10.

The processing module 12 is configured to generate the sound wave signal towards the liner L and receive the sound wave signal detected by the matching layer 111, and measure a thickness of the liner L based on the received sound wave signal and transfer data of the measured thickness of the liner L to an outside. Through such a structure, the sound wave signal generated from the processing module 12 is transferred to the liner L, and is then reflected from the liner L and detected by the transducer 11. Subsequently, the processing module 12 is configured to analyze the detected sound wave signal and obtain the data of the thickness of the liner L based on a speed of the sound wave signal and an amount of time used, and then transfer the obtained data to an outside such that an operator (e.g., surgeon) or a user (e.g., patient) may verify a life of the artificial joint, or a life of the liner L. Thus, it is possible to readily verify a replacement period of the artificial joint.

The processing module 12 includes a sound wave transmitter-receiver 121, a processor 122, a data transmitter-receiver 123, and a power unit 124.

The sound wave transmitter-receiver 121 includes a sound wave signal transmitter 1211 configured to generate the sound wave signal and transfer the generated sound wave signal to the liner L, and a sound wave signal receiver 1212 configured to receive the sound wave signal reflected from the liner L through the transducer 11.

The processor 122 is configured to analyze the sound wave signal received from the sound wave signal receiver 1212 and obtain the data of the thickness of the liner L. Here, the sound wave signal may be predetermined, and the thickness of the liner L may be measured based on a preset speed of the sound wave signal, and on an amount of time used from a point in time at which the sound wave signal is generated from the sound wave signal transmitter 1211 and then reflected from the liner L, to a point in time at which the reflected sound wave signal is received by the sound wave signal receiver 1212. In addition, the processor 122 is configured to control power to assist the processing module 12 in performing its operations.

The data transmitter-receiver 123 includes a wireless data receiver 1231 configured to receive the data of the thickness of the liner L from an outside, and a wireless data transmitter 1232 configured to transmit the data of the thickness of the liner L to an outside. Each of the wireless data receiver 1231 and the wireless data transmitter 1232 is connected to the processor 122 to exchange data processed by the processor 122, and includes therein a wireless communication module to communicate with an outside.

The power unit 124 includes a wireless power receiver 1241 configured to receive power, and a power controller 1242 configured to allow the processor 122 to control the power. Through such a structure, even when the smart screw 1 is inserted in the hip joint O of the object and fixed thereto, the operator or the user may obtain the data of the thickness of the liner L of the artificial joint by receiving power noninvasively without an invasive procedure.

The coil 13 is disposed in the main screw body 10 to surround the piezoelectric layer 112, and configured to transmit or receive an electromagnetic wave to or from an outside. A coil 15 may be installed in an external structure such as the shell C and the liner L, in addition to inside the main screw body 10. In such a case, the smart screw 1 further includes a connection member configured to connect the coil 15 and the transducer 11 in the main screw body 10. In addition, the coil 13 is connected to the data transmitter-receiver 123, and configured to transmit data and power received from an outside to the data transmitter-receiver 123 and the power unit 124, respectively. For example, the coil 13 may receive or transmit, from or to an outside, data and power in a form of electromagnetic wave. Through such a structure, the coil 13 is not connected to a power source, and thus it is possible to operate the smart screw 1 by generating an electromagnetic wave whenever needed. In addition, a separate power source is not needed, and thus it is possible to maintain an existing size of a screw and use the screw to fix a generally used artificial joint without a need to an additional device or structure.

The transmitting layer 14 is configured to allow an electromagnetic wave to be transmitted to communicate with the coil 13. Thus, the transmitting layer 14 is formed on an outer side of the main screw body 10 to surround the transducer 11 and the processing module 12. Through such a structure, the transmitting layer 14 may absorb most of electromagnetic waves from an outside while protecting the main screw body 10 against an external impact, and transfer the absorbed electromagnetic waves to the processing module 12. Thus, a data transmission and reception rate may be improved.

Figure 3:
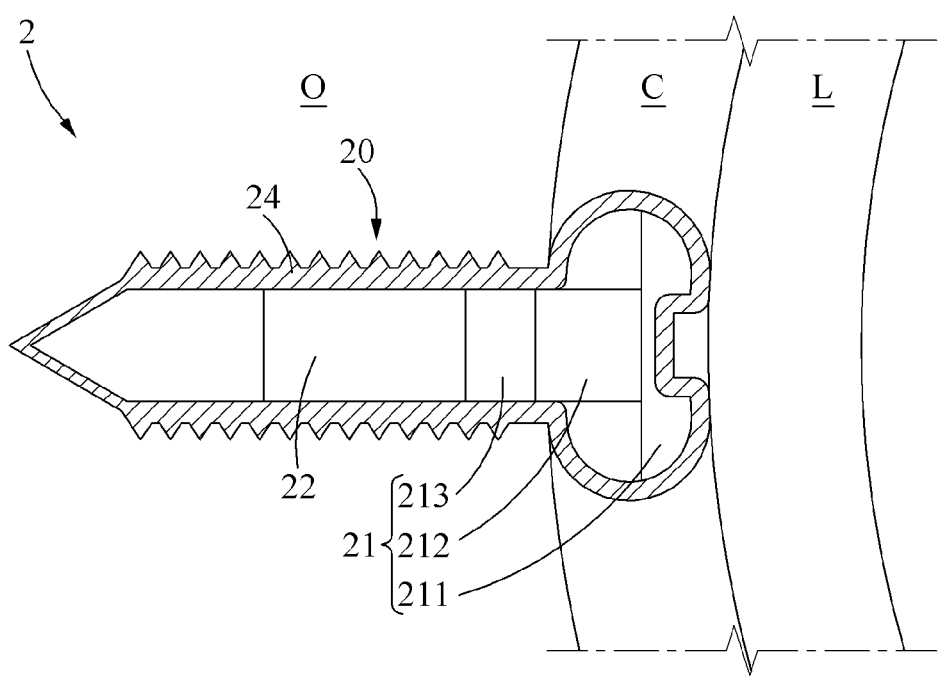
FIG. 3 is a cross-sectional view of an example of a smart screw according to an example embodiment.
Figure 4:
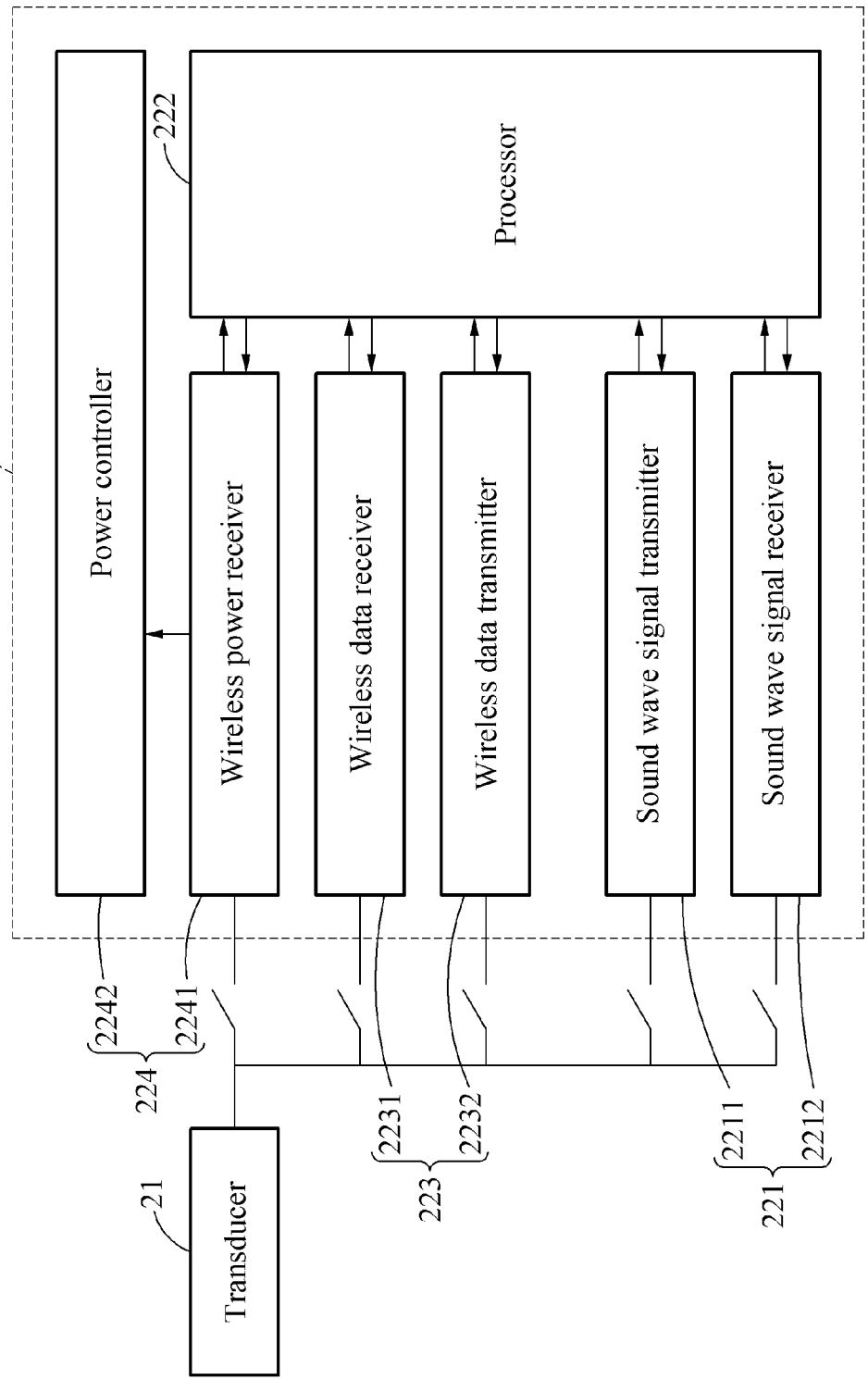
FIG. 4 is a conceptual view of an example of a smart screw according to an example embodiment.

FIG. 3 is a cross-sectional view of an example of a smart screw according to an example embodiment. FIG. 4 is a conceptual view of an example of a smart screw according to an example embodiment.

Referring to FIGS. 3 and 4, a smart screw 2 includes a main screw body 20 configured to penetrate an artificial joint including a shell C disposed in a hip joint O of an object and a liner L disposed on an inner surface of the shell C to be inserted into the hip joint O, a transducer 21, a processing module 22, and a transmitting layer 24.

The transducer 21 is disposed in the main screw body 20. The transducer 21 includes a matching layer 211 disposed inside the main screw body 20 in the vicinity of the liner L, a piezoelectric layer 212 disposed in the vicinity of the matching layer 211, and a backing layer 213 disposed in the vicinity of the piezoelectric layer 212. The transducer 21 is configured to detect a sound wave signal reflected from the liner L, and also receive power transferred in a form of electromagnetic wave.

The processing module 22 is connected to the transducer 21, and configured to measure a thickness of the liner L based on the sound wave signal and transfer the data of the measured thickness of the liner L to an outside. The processing module 22 includes a sound wave transmitter-receiver 221, a processor 222, a data transmitter-receiver 223, and a power unit 224.

In a case in which a transmission efficiency of a coil capable of transmitting power is not relatively high, an operation efficiency of the smart screw 2 may be degraded. In such a case, the transducer 21 may receive power in a form of electromagnetic wave, in addition to detect the sound wave signal reflected from the liner L, without using the coil. Thus, it is possible to improve a spatial efficiency of the smart screw 2.

Figure 5:
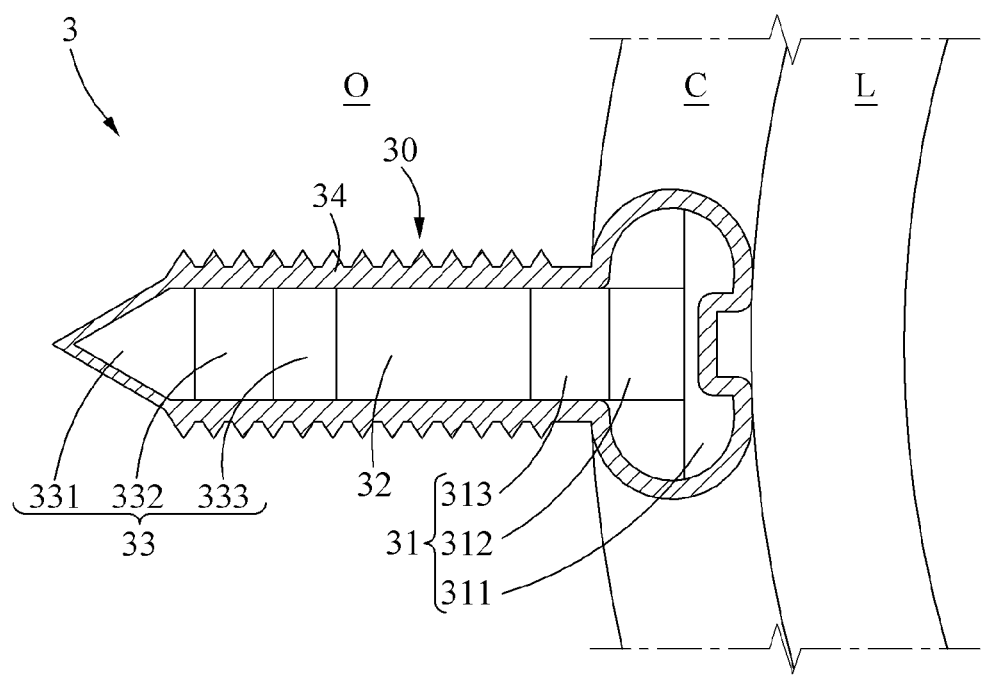
FIG. 5 is a cross-sectional view of an example of a smart screw according to an example embodiment.
Figure 6:
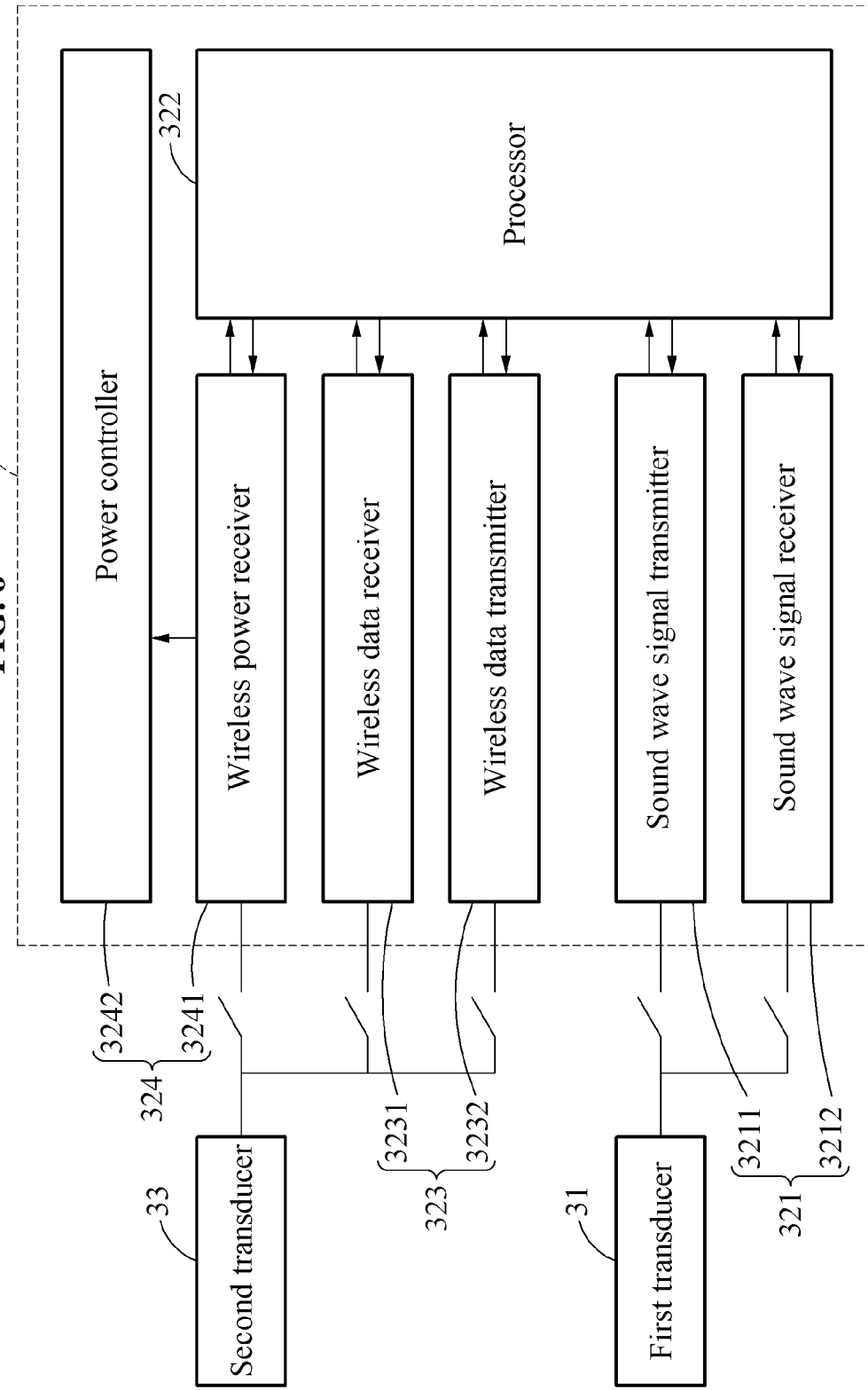
FIG. 6 is a conceptual view of an example of a smart screw according to an example embodiment.

FIG. 5 is a cross-sectional view of an example of a smart screw according to an example embodiment. FIG. 6 is a conceptual view of an example of a smart screw according to an example embodiment.

A smart screw 3 includes a main screw body 30 configured to penetrate an artificial joint including a shell C disposed in a hip joint O of an object and a liner L disposed on an inner surface of the shell C to be inserted into the hip joint O, a first transducer 31, a processing module 32, and a second transducer 33. The processing module 32 includes a sound wave transmitter-receiver 321, a processor 322, a data transmitter-receiver 323, and a power unit 324. In detail, the first transducer 31 is connected to the sound wave transmitter-receiver 321, and the second transducer 33 is connected to each of the data transmitter-receiver 323 and the power unit 324.

The first transducer 31 is configured to detect a sound wave signal reflected from the liner L. Thus, the first transducer 31 is disposed at a proximal end of the main screw body 30 in the vicinity of the linear L. The first transducer 31 includes a first matching layer 311, a first piezoelectric layer 312, and a first backing layer 313. The second transducer 33 is configured to receive power from an outside. Thus, the second transducer 33 is disposed at a distal end of the main screw body 30 by being separate from the first transducer 31. The second transducer 33 includes a second matching layer 331, a second piezoelectric layer 332, and a second backing layer 333.

The first piezoelectric layer 312 of the first transducer 31 is formed to have a first frequency band of the sound wave signal. For example, a thickness of the first piezoelectric layer 312 may be determined to have the first frequency band, for example, an ultrasonic wave band for high frequency, of the sound wave signal. The second piezoelectric layer 332 of the second transducer 33 is formed to have a second frequency band of the sound wave signal. For example, a thickness of the second piezoelectric layer 332 may be determined to have the second frequency band, for example, an ultrasonic wave band for low frequency, of the sound wave signal.

When receiving power while detecting a sound wave signal reflected from a liner L by a single transducer 31 or 33, an efficiency of one of a function of detecting a sound wave signal and a function of receiving power may be degraded because a frequency for detecting a sound wave signal needs to be higher than a frequency for receiving power. Thus, through such a structure, by disposing the first transducer 31 to be adjacent to the liner L, and disposing the second transducer 33 to be separate from the first transducer 31, the different functions may be performed in different frequency bands. Thus, it is possible to independently perform functions of the first transducer 31 and the second transducer 33, and thus an operation efficiency of the smart screw 3 may be improved.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

The invention claimed is:

1. A smart screw comprising:
   a main screw body configured to penetrate an artificial joint, the artificial joint including a shell configured to be disposed on a joint of an object and a liner disposed on an inner surface of the shell, and configured to be inserted into the joint;
   a transducer including a matching layer configured to detect a sound wave signal reflected from the liner, a piezoelectric layer formed to have a preset frequency of the sound wave signal, and a backing layer configured to absorb the sound wave signal; and
   a processing module configured to generate the sound wave signal towards the liner, receive the sound wave signal detected by the matching layer, measure a thickness of the liner based on the received sound wave signal, and transfer data of the measured thickness of the liner to a location outside of the smart screw.

2. The smart screw of claim 1, further comprising:
   a coil disposed to surround the piezoelectric layer, and configured to transmit or receive an electromagnetic wave to or from the location outside of the smart screw.

3. The smart screw of claim 2, wherein the processing module includes:
   a sound wave transmitter-receiver configured to generate the sound wave signal and transfer the generated sound wave signal to the liner, and receive the sound wave signal reflected from the liner through the transducer;
   a processor configured to analyze the received sound wave signal and obtain the data of the thickness of the liner, and control power;
   a data transmitter-receiver configured to transmit and receive the data of the thickness of the liner to and from the location outside of the smart screw through the coil; and
   a power unit configured to receive power through the coil and allow the processor to control the power.

4. The smart screw of claim 2, further comprising:
   a transmitting layer formed on an outer side of the transducer and the processing module, and configured to allow the electromagnetic wave to be transmitted to communicate with the coil.

5. The smart screw of claim 1, further comprising:
   a coil located outside of the smart screw and designed and configured to be located in at least one component of the artificial joint, wherein the coil is connected to the transducer, and configured to transmit or receive an electromagnetic wave to or from the location outside of the smart screw.

6. The smart screw of claim 1, wherein the joint is a hip joint, a pelvic joint, a knee joint, an elbow joint, or an ankle joint.

7. The smart screw of claim 1, wherein the processing module is disposed in the smart screw.

8. A smart screw comprising:
   a main screw body configured to penetrate an artificial joint including a shell disposed on a joint of an object and a liner disposed on an inner surface of the shell to be inserted into the joint;
   a transducer disposed in the main screw body, and configured to detect a sound wave signal generated by the smart screw and reflected from the liner and receive power from a location outside of the smart screw; and
   a processing module connected to the transducer, and configured to measure a thickness of the liner based on the sound wave signal and transfer data of the measured thickness of the liner to the location outside of the smart screw.

9. The smart screw of claim 8, wherein the processing module includes:
   a sound wave transmitter-receiver configured to generate the sound wave signal and transfer the generated sound wave signal to the liner, and receive the sound wave signal reflected from the liner through the transducer;
   a processor configured to analyze the received sound wave signal and obtain the data of the thickness of the liner, and control power;
   a data transmitter-receiver configured to transmit and receive the data of the thickness of the liner to and from the location outside of the smart screw through the transducer; and
   a power unit configured to receive power through the transducer and allow the processor to control the power.

10. The smart screw of claim 8, wherein the joint is a hip joint, a pelvic joint, a knee joint, an elbow joint, or an ankle joint.

11. The smart screw of claim 8, wherein the processing module is disposed in the smart screw.

12. A smart screw comprising:
   a main screw body configured to penetrate an artificial joint including a shell disposed on a joint of an object and a liner disposed on an inner surface of the shell to be inserted into the joint;
   a first transducer disposed on a proximal end of the main screw body;
   a second transducer disposed on a distal end of the main screw body; and a processing module connected to each of the first transducer and the second transducer, and configured to obtain data of a thickness of the liner and transmit and receive power to and from a location outside of the smart screw.

13. The smart screw of claim 12, wherein the first transducer is configured to detect a sound wave signal reflected from the liner, and the second transducer is configured to receive power from the outside.

14. The smart screw of claim 13, wherein the first transducer includes a first piezoelectric layer formed to have a first frequency band of the sound wave signal, and the second transducer includes a second piezoelectric layer formed to have a second frequency band of the sound wave signal.

15. The smart screw of claim 12, wherein the processing module includes:

a sound wave transmitter-receiver configured to generate a sound wave signal and transfer the generated sound wave signal to the liner, and receive the sound wave signal reflected from the liner through the first transducer;

a processor configured to analyze the received sound wave signal and obtain the data of the thickness of the liner, and control power;

a data transmitter-receiver configured to transmit and receive the data of the thickness of the liner to and from the outside through the second transducer; and a power unit configured to receive power through the second transducer and allow the processor to control the power.

16. The smart screw of claim 12, wherein the joint is a hip joint, a pelvic joint, a knee joint, an elbow joint, or an ankle joint.

* * * * *